United States Patent [19]

Lessard et al.

[11] 4,441,369
[45] Apr. 10, 1984

[54] ULTRASONIC DETECTION OF EXTENDED FLAWS

[75] Inventors: Dennis E. Lessard, Waterford; Paul F. Sabourin, Scotia, both of N.Y.

[73] Assignee: General Electric Company, Schenectady, N.Y.

[21] Appl. No.: 429,710

[22] Filed: Sep. 30, 1982

[51] Int. Cl.³ .............................................. G01N 29/04
[52] U.S. Cl. ...................................... 73/602; 73/620; 73/623
[58] Field of Search ................. 73/602, 618, 620, 622, 73/623, 627, 629

[56] References Cited

U.S. PATENT DOCUMENTS 4,054,053 10/1977 Yamamoto et al. .................. 73/620
4,226,122 10/1980 Lund et al. ............................ 73/620

*Primary Examiner*—James J. Gill
*Attorney, Agent, or Firm*—John F. Ahern; Robert C. Kain, Jr.

[57] ABSTRACT

An extended flaw in a material is located in two or three dimensions by propagating ultrasonic energy in a predetermined direction in the material and logging receiving transducer positions and ranges at which individual facets on the surface of the flaw produce maximum amplitude ultrasonic returns. The positions of all of the individual facets in the material are calculated from the predetermined direction, receiving transducer positions and the corresponding ranges. The locations of the individual facets outline the extended flaw.

15 Claims, 9 Drawing Figures

ULTRASONIC DETECTION OF EXTENDED FLAWS

BACKGROUND OF THE INVENTION

The present invention relates generally to flaw detection in solid materials and, more particularly, to flaw detection employing non-destructive testing techniques.

Non-destructive testing to identify and/or isolate flaws or discontinuities in solid materials have typically employed X-ray and ultrasonic techniques among others. X-ray techniques, although providing relatively complete information about the extent of flaws in solid materials such as metal, require that the metal structure be in a form which permits the X-rays to pass completely therethrough from X-ray source to film. In the case of very thick sections of metal, exposure times and dynamic range interfere with obtaining good data. In addition, X-ray testing is time consuming and costly.

Monostatic pulse-echo ultrasonic testing techniques, wherein transmitting and receiving transducers are generally collocated, have been successfully employed in the detection of flaws in critical objects such as the rotors of turbines and generators. Such use is disclosed in a paper entitled, "Boresonic Inspection of Forged Turbine and Generator Rotors" by W. R. Marklein and R. E. Warnow presented to the American Society of Mechanical Engineers at its annual meeting in New York, Nov. 29 to Dec. 4, 1964. In this report, a pulse-type ultrasonic transducer launches pulses of ultrasonic vibration into a forging from within an axial bore. Cracks, tears or non-metallic inclusions in the forging produce discontinuities which reflect the ultrasonic energy to the receiving transducer. The received reflected ultrasonic energy cannot be directly correlated with the actual size of the flaw. However, in the absence of better techniques for testing large forgings in critical applications, the above ultrasonic methods have been developed into a commercial operation and routinely applied in the non-destructive testing of large turbine and generator forgings.

Flaws fall into two general classifications, namely point flaws and extended flaws. Point flaws, which may be due to porosity or small non-metallic inclusions, have dimensions which are too small to provide more than a single indication to an ultrasonic sensor. Extended flaws have dimensions large enough so that a plurality of resolvable indications may be received.

One of the reasons that the ultrasonic return from an extended flaw is poorly correlated with the size of the flaw is that the reflection of ultrasonic energy from a flaw is fairly critically dependent on the angular relationships of the direction of propagation of the ultrasonic energy and the orientation of the flaw. Maximum ultrasonic return is achieved when the flaw is disposed normal to the direction of propagation of the ultrasonic energy. Thus, a very large return may be obtained from a relatively small crack fortuitously disposed normal to the direction of propagation of the ultrasonic energy whereas a relatively small return may be received from a relatively large and serious flaw disposed at an oblique angle to the direction of propagation of the ultrasonic energy.

The term ultrasonic is generally taken to mean mechanical vibration at frequencies higher than the audible range. That is, higher than about 20 KHz. For non-destructive testing in metals, ultrasonic frequencies in the range of from about 1 to about 10 MHz are customarily employed.

OBJECTS AND SUMMARY OF THE INVENTION

Accordingly, it is an object of the invention to provide a method for sensing the extent of flaws in a solid object.

It is a further object of the invention to provide a method for analyzing the data from an ultrasonic flaw detector to provide information about the extent and seriousness of flaws in a solid object.

It is a further object of the invention to provide a method for determining the shape and size of an interface between sound material and an extended flaw based on the relationship between amplitude of an ultrasonic return echo and a sensor position at which the echo is received.

It is a further object of the invention to provide apparatus for analyzing reflections of ultrasonic energy to define an extended flaw in a solid body.

According to an aspect of the present invention, there is provided a method for defining an extended flaw in a body, comprising propagating a beam of pulses of vibratory energy from a plurality of points on a surface of the body at a predetermined angle into the body, the vibratory energy being of a type which may be reflected at the extended flaw, detecting reflected vibratory energy at the plurality of points, determining that a plurality of peaks of the reflected vibratory energy occur within a predetermined time at each of a plurality of adjacent ones of the plurality of points, correlating the plurality of peaks at least three adjacent ones of the plurality of points, defining as a search point for the one of the peaks the one of the plurality of points at which a maximum amplitude of one of the peaks exists, logging the search point and a range to a facet producing the maximum amplitude, continuing the steps of defining and logging for a substantial number of others of the peaks, and calculating locations of facets within the body producing the maximum amplitudes of the one and the substantial number of others of the peaks based on the predetermined angle, the search points and measured ranges from each of the search points.

According to a further aspect of the present invention, there is provided a method for defining an extended flaw in a body, comprising scanning an ultrasonic transducer along a path on a surface of the body, transmitting pulses of ultrasonic energy into the body from the transducer at a predetermined angle with respect to the surface, receiving reflections of the ultrasonic energy at the surface along the path, defining a group of peaks of reflections of ultrasonic energy received within a predetermined time and moving together in range during the scanning as originating along a surface of the extended flaw, determining the points along the path at which ones of the peaks reach maximum amplitude, measuring a range from each of the points to a facet producing its maximum amplitude reflection, and calculating positions of each of the facets in the body based on the predetermined angle, locations of the points and corresponding ranges to the facets, the facets defining points on the extended flaw.

According to a feature of the present invention, there is provided an apparatus for processing ultrasonic reflections from a body to define an extended flaw, in which transmitting and receiving transducers are moved in a scan on a surface of the body, comprising means for determining that a plurality of peaks of the ultrasonic reflections are received within a predetermined time, means for correlating the peaks as the transmitting and receiving transducers are moved in the scan, means for determining points along the path at which ones of the peaks are maximum, and means for logging the points and ranges associated with the points, the points and ranges together with a predetermined propagation angle of ultrasonic energy in the body are usable to calculate positions of facets defining a surface of the extended flaw.

According to a further feature of the present invention, there is provided a method for defining extended flaws in a rotor of the type having an axial bore therein, comprising scanning receiving and transmitting transducers of ultrasonic energy in one of a circumferential and an axial direction in the axial bore and incrementing the transducers in the other of the directions, the transmitting transducer propagating ultrasonic energy at a predetermined angle in the body, measuring ranges of reflections of ultrasonic energy, determining that a predetermined plurality of the reflections are within a predetermined distance of each other, finding search positions of the transducers producing maximum amplitudes of individual ones of the reflections, calculating positions of facets on the extended flaw based on the predetermined angle, the search positions and corresponding ranges, and the facets defining the extended flaw.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Flaws in metallic forgings and other solid objects may be small, discrete, unresolvable points due to porosity in the material or may extend for a substantial distance. Resolution of extended flaws depends on the relationship between the wavelength of the ultrasonic energy in the material and the linear extent of the flaw. The wavelength of ultrasonic energy is as follows:

$$\lambda = v/f$$

Where:
$\lambda$ = wavelength
v = velocity of sound in the material
f = frequency In metals, the velocity of sound v is from about 3,000 to about 8,000 meters per second. Ultrasonic frequencies from about 0.4 to about 10 MHz may be employed. For purposes of comparison, a velocity of sound of about 7,000 meters per second and a frequency of about 5 MHz give a wavelength $\lambda$ of about 1.4 mm. Thus, if the extent of the flaw or inclusion exceeds about 1 or 2 mm, there is a possibility that the flaw or inclusion may be resolved as having a measurable extent rather than as a point scatterer.

The method of the present invention depends on two fundamental properties of flaws or inclusions: (1) that there is an interface between the material and the flaw; and (2) the interface offers a substantial number of facets relatively close together which may or may not be oriented normal to the direction of propagation of the ultrasonic energy thus providing local peaks of ultrasonic reflection.

Although the applicants do not tend to be bound by any particular theory, it can be observed that cracks and inclusions in metal very frequently follow grain boundaries or other irregular paths so that there are large variations in surface orientation of facets over relatively small linear distances. Statistically, a substantial number of these facets can be normal to the direction of propagation of the ultrasonic energy.

Ultrasonic transducers typically produce longitudinal ultrasonic vibration. When this longitudinal ultrasonic vibration is coupled into the surface of the material at transducer angles within about 25° of the normal, predominantly longitudinal ultrasonic waves are propagated in the body. At transducer angles between about 25° and 55° from the normal, predominantly shear ultrasonic waves are propagated in the body. At transducer angles between 55° and 70° from the normal, surface waves are propagated. The applicants contemplate that either longitudinal or shear propagation modes are capable of accomplishing generally comparable results and, for purposes of the present invention, either of these propagation mode may be employed. For purposes of concreteness of description, it will be assumed that the ultrasonic transducer is arranged with its axis between 30° and 50° to the normal and thus propagates shear waves within the material.

Figure 1:
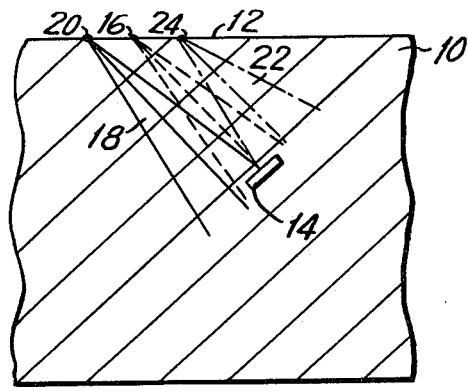
FIG. 1 is a cross sectional diagram of a body of material containing a planar flaw to which reference will be made in explaining the principle of the present invention.

Referring now to FIG. 1, the basic principle of the method is illustrated. A metallic body 10, having a plane surface 12, includes a single small planar flaw 14 within it. A normal to the plane of planar flaw 14 cuts surface 12 at a point 16. If ultrasonic energy is propagated along the normal line from point 16, planar flaw 14 is ideally disposed to reflect a maximum amount of ultrasonic energy back to a receiving transducer (not shown) located at point 16.

In fact, however, ultrasonic transmission into a body is not accomplished along a line of infinite thinness. Instead, ultrasonic energy is propagated in a cone having maximum energy on the axis of the cone and reducing away from the axis. Thus, a cone 18 of ultrasonic energy projected into body 10 from a transducer located at a point 20 spaced apart from ideal point 16 projects ultrasonic energy onto planar flaw 14. However, since planar flaw 14 is not disposed normal to the incidence of the portion of ultrasonic energy reaching it in cone 18, the amplitude of the echo signal received at point 20 is substantially smaller than the amplitude that is received at point 16 which is ideally situated for normal incidence. Similarly, ultrasonic energy projected into body 10 in a cone 22 from a point 24 results in reflection of a lower amplitude return at point 24 from planar flaw 14. Thus, if a source and detector are scanned through points 20, 16 and 24, the amplitude of the received signal reaches a maximum at point 16 and decreases on either side.

A further phenomenon to be noted is that the distances from points 20, 16 and 24 to planar flaw 14 are slightly different. Thus, as a transducer is moved on surface 12 from point 20 through point 16 to point 24, a distance indication to planar flaw 14 changes. The peak signal return received at point 16 identifies point 16 as the search point defining the position of planar flaw 14. The known angle of propagation of the ultrasonic beam together with the measured distance from point 16 to planar flaw 14 fixes the location of flaw 14 in body 10.

Although the preceding method is not exactly rigorous since it depends on fortuitous angular positioning of the plane of planar flaw 14, the applicants have discovered that this method provides more precision in the location of flaws than was previously available with ultrasonic techniques.

The preceding discussion of the method of detecting a single flaw provides the basis for understanding the method for detecting extended flaws, cracks and non-metallic inclusions.

Figure 2:
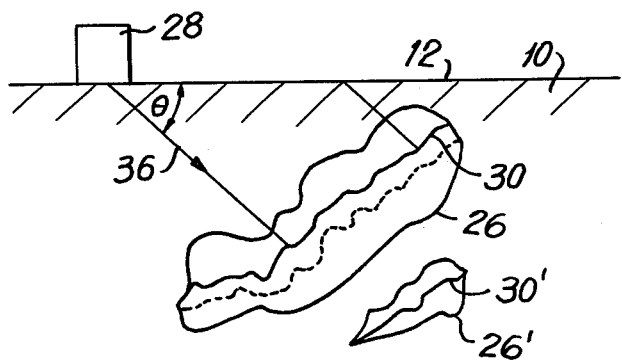
FIG. 2 is a cross section of a body including two flaws each having substantial extent in three dimensions.

Referring now to FIG. 2, a body 10 includes an extended flaw 26 having a substantial extent in three dimensions and having a characteristic irregular interface with the remainder of metallic body 10. An ultrasonic transducer 28 projects a beam of ultrasonic energy having a beam axis at an angle $\theta$ from surface 12 into body 10. Due to the irregular shape of the interface of flaw 26, the axis of ultrasonic energy traces out an irregular line 30 on flaw 26.

Figure 3:
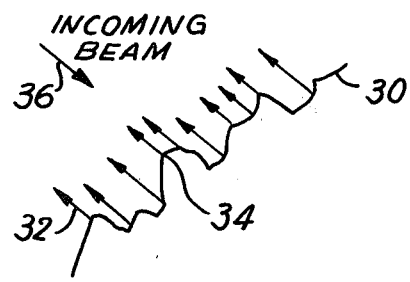
FIG. 3 is an enlarged view of an irregular line of a flaw showing the plurality of facets which can exist normal to an incoming ultrasonic beam.

Referring momentarily to FIG. 3, a closeup of irregular line 30 is shown. Arrows 32 identify a plurality of points or facets 34 on line 30 which are disposed normal to incoming beam 36 of ultrasonic energy. In moving in a scan from left to right, incoming beam 36 periodically lines up with one of normal facets 34 to produce a peak in reflected energy. The applicants have discovered that an extended flaw typically disposes two, three or more facets 34 within the effective cone (not shown) surrounding the axis of beam 36 thus simultaneously providing returns to the receiving transducer. In a typical case, the several points 34 simultaneously providing returns are at different ranges and it is possible to separately track each one of points 34 as the transducer position is changed.

Any convenient method of displaying and storing range, amplitude and transducer position data may be employed. For example, the data may be suitably conditioned and stored in a computer memory with the computer performing post-detection processing to identify actual flaw positions. Alternatively, a suitable display may be presented to an operator who observes the amplitudes and ranges as the ultrasonic transducer position changes and logs the ranges and transducer positions associated with the peak amplitudes.

The operator applies the following criteria to identify and trace an extended flaw:
1. Two or more local peaks exceeding a threshold must appear as a group within 10 microseconds and preferably within 5 microseconds of each other.
2. All members of the group must appear to move in range as the transducer position is swept.
3. Each member must remain above the threshold for at least a minimum predetermined transducer position change.

Figure 4A:
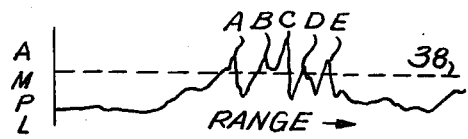
FIGS. 4A–4C are A-scope presentations of a detected ultrasonic return at three different positions of an ultrasonic transducer.
Figure 4B:
Figure 4C:
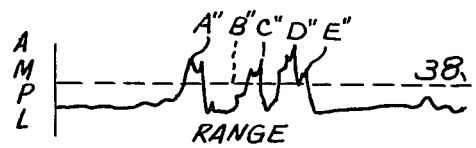

For illustration of this process, A-scope presentations of the acoustic returns received at three succeeding positions of the transducer are shown in FIGS. 4A, 4B and 4C. An A-scope presentation, conventionally displayed on a cathode ray tube, consists of a trace of amplitude on the vertical axis versus range or time on the horizontal axis. In FIG. 4A, peaks A, B, C, D and E exceed threshold 38. In FIG. 4B, the ranges and amplitudes of corresponding points are shown at A', B', C', D' and E'. It will be noted that the amplitude of A' exceeds the amplitude of A. In addition, the amplitude of C' is less than the amplitude of C. In addition, all of the ranges are reduced in FIG. 4B. The reduction in range of all peaks is not universal since it is possible for the ranges of some peaks to be increasing while the ranges of other are decreasing depending on the orientation and shape of the flaw.

In FIG. 4C, A" is of lower amplitude than A'. Thus, the position of FIG. 4B is accepted as defining the position of facet A of the flaw. B' is below the threshold and thus this point is discarded. C in FIG. 4A is of greater amplitude than the amplitudes of C' and C". Since C may or may not represent a maximum depending on the return from a transducer position beyond the one producing the display in FIG. 4A, no conclusion can be reached without further sweep of the transducer D" in FIG. 4C exceeds D' and D thus, no conclusion can be reached without extending the sweep. Finally, E, E' and E" do not show sufficient change in amplitude to define a peak.

The three search locations or points represented by signal returns in FIGS. 4A, 4B and 4C may be defined by equal increments of motion of the transducer along the surface. In the preferred embodiment, however, a search location is defined as that location at which the maximum amplitude of a particular peak is received. Thus, in general, the search locations are disposed at irregular intervals along a sweep. That is, an operator viewing the display of FIGS. 4A-4C moves the transducer location until one of the peaks in the return signal actually reaches its maximum amplitude and then logs the transducer location producing this result as well as the range.

Figure 5:
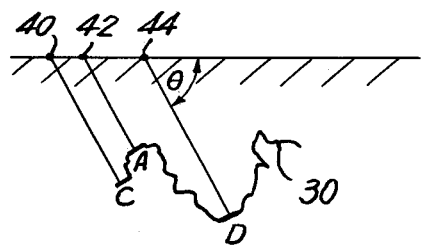
FIG. 5 is a cross section of a body showing three of the facets located in the A-scope presentations of FIGS. 4A–4C and the transducer locations defining the positions of the flaws.

Referring to FIG. 5, for example, facets C, A and D located on line 30, produce maximum amplitude signals at transducer search points 40, 42 and 44. Given the known angle $\theta$, search points 40, 42 and 44 and the respective ranges, an operator can plot or otherwise record the positions of facets C, A and D as well as all other facets along line 30. The positions of the individual facets can be graphically connected to provide a trace closely approximating the actual shape and position of irregular line 30. Additional transducer scans parallel to the scan previously described can be employed to permit plotting the flaw in three dimensions.

If the data are being stored and analyzed by computer, a continuous process may be performed in which computer analysis tracks each peak, ensures that each peak is a member of a group that has endured for a sufficient period and has appropriately moved in range during the transducer scan in a manner to be classified as a real signal and automatically logs the transducer search position and range corresponding to maximum amplitude. The range, angle and transducer search position are thereupon used to pinpoint the actual position of the facet within the body and the collection of detected facets are used to trace out the flaw.

Although it may overtax the ability of a human operator to perform, the present invention is usable on multiple flaws simultaneously visible to the ultrasonic energy. That is, a second flaw 26' (FIG. 2) located at a point where it may be sensed simultaneously with flaw 26 may exist in body 10. It would be clear to one skilled in the art that computer storage and processing would be capable of separating returns along irregular lines 30 and 30' in flaws 26 and 26' and thereby calculating the extent of these flaws even though they overlap on the line of sight from transducer 28. The ability to perform this detection of multiple flaws depends, of course, on whether or not the nearest flaw permits sufficient ultrasonic energy to pass through it, reflect from facets in the further flaw and then return to transducer 28.

The invention is not limited to monostatic ultrasonic systems. A bistatic system with transmitting and receiving transducers separated from each other, is equally within the contemplation of the applicants. In a bistatic system, maximum amplitude reflection is received when the angles of incidence and reflection of ultrasonic energy on a facet are equal.

Figure 6:
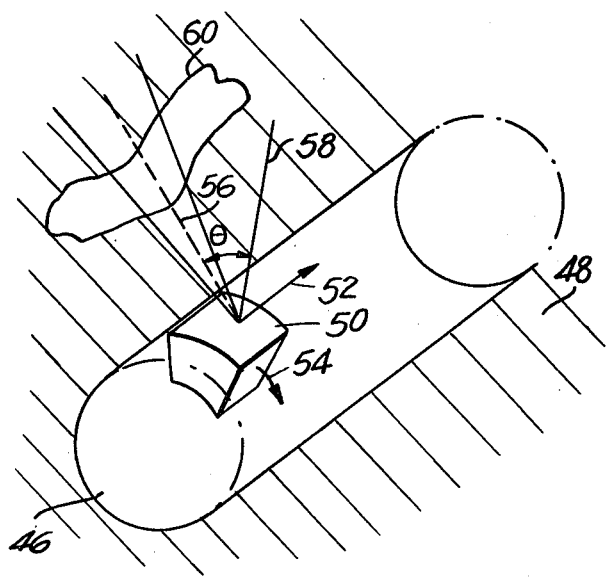
FIG. 6 is a cross section of a rotor having a bore therein with an ultrasonic transducer scannable in the bore to detect flaws.

The preceding description has employed a body with a plane surface for simplifying the introduction to the method. The method is fully applicable to such use but is not limited to use with plane surfaces or simple shapes. In particular, the preceding description is fully applicable to the testing of rotors for turbines and generators wherein the transducer is disposed within an axial bore in the rotor. FIG. 6 shows a cross section of this application wherein a bore 46 in a rotor 48 has an ultrasonic transducer 50 inserted therein and scanned in an axial direction, as indicated by an arrow 52 as well as in a circumferential direction as indicated by a curved arrow 54. A beam 56 of ultrasonic energy is projected into rotor 48 at an angle $\theta$ from a normal 58 whereby either longitudinal or shear waves are produced for beam 56. As in the preceding discussion, the three-dimensional position of a flaw 60 is traced out by the positions of facets on the flaw.

In a manual system, ultrasonic transducer 50 is incremented in one direction and then scanned in the second direction. That is, ultrasonic transducer 50 may be fixed in the circumferential direction 54 and scanned in the axial direction 52 or vice versa. In the preferred embodiment of a manual system, ultrasonic transducer 50 is incremented in the axial direction 52 and is circumferentially scanned. In an automatic system employing computer data storage and reduction, a helical scan of ultrasonic transducer 50 is preferred wherein simultaneous smooth motion in both circumferential 54 and axial directions 52 is performed.

Figure 7:
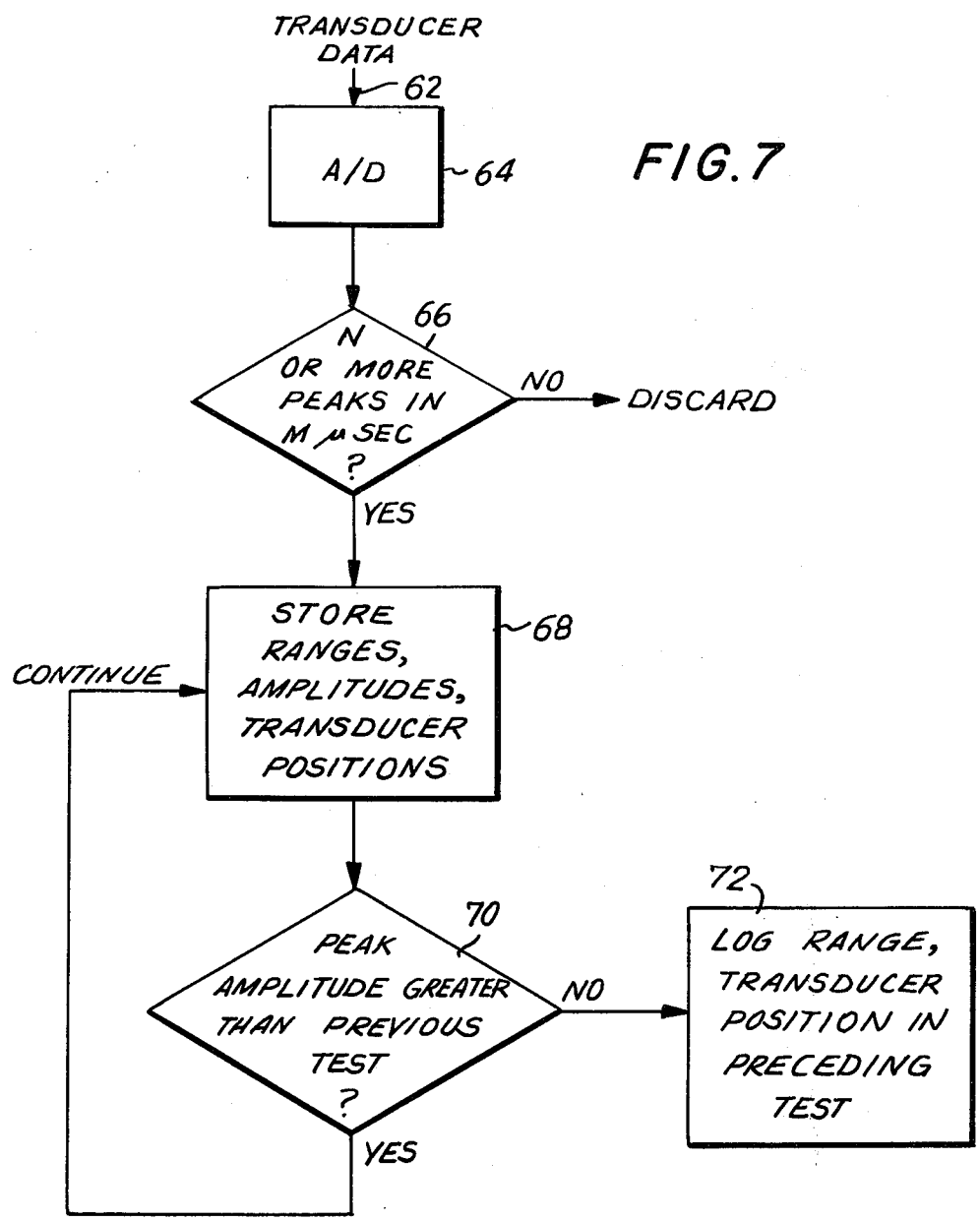
FIG. 7 is a bare bones flow chart of a computer program to automatically detect and log positions of facets returning peak ultrasonic energy and defining points on the flaw.

Referring now to FIG. 7, a bare bones flow chart is shown of a computer method for performing the analysis. Transducer data including transducer position, echo amplitude data and range is applied on a line 62 to an A/D converter 64 where the incoming data is converted from analog to digital. The digitized data is applied to a decision element 66 which determines whether or not N or more peaks occur in M microseconds of the transducer signal. If decision element 66 finds less than N peaks in M microseconds, any data contained therein is discarded. If N or more peaks are located in M microseconds of data, the corresponding ranges, amplitudes and transducer positions are stored in a memory 68. As each set of new data is stored in memory 68, the amplitude of each peak is compared with its amplitude in previous tests. If the present peak amplitude is less than the preceding peak amplitude, this indicates that the peak has been passed. In this event, a decision element 70 enables logging of the range and transducer position from the immediately preceding test in a register 72. If the present peak amplitude is greater than the amplitude in the previous test, indicating that the maximum has not yet been passed, decision element 70 enables memory 68 to continue storing and providing new samples of a particular peak.

It would be clear to one skilled in the art that memory 68 must identify and track individual peaks as they change in range with changing transducer position in order to be able to compare amplitudes from test to test. Range tracking of this nature is conventional in the radar and sonar arts, for example, and will not be treated in detail herein.

The flow chart of FIG. 7 may be executed by any convenient digital processing equipment including main frame computers, mini computers but, in the preferred embodiment, the program is executed in a microprocessor and is preferably performed in real time. It would be clear that digital processing is not a necessity since analog processing may be employed for most, if not all of the functions.

Having described specific preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

We claim:

1. A method for defining an extended flaw in a body, comprising:
   propagating a beam of pulses of vibratory energy from a plurality of points on a surface of said body at a predetermined angle into said body, said vibratory energy being of a type which may be reflected at said extended flaw;
   detecting reflected vibratory energy at said plurality of points;
   determining that a plurality of peaks of said reflected vibratory energy occur within a predetermined time at each of a plurality of adjacent ones of said plurality of points;
   correlating said plurality of peaks at at least three adjacent ones of said plurality of points;
   defining as a search point for said one of said peaks the one of said plurality of points at which a maximum amplitude of one of said peaks exists;
   logging said search point and a range to a facet producing said maximum amplitude;
   continuing the steps of defining and logging for a substantial number of others of said peaks; and
   calculating locations of facets within said body producing said maximum amplitudes of said one and said substantial number of others of said peaks based on said predetermined angle, said search points and measured ranges from each of said search points.

2. A method according to claim 1, wherein said vibratory energy is ultrasonic energy.

3. A method according to claim 1, wherein the step of propagating a beam includes scanning said beam along a path on said surface through said plurality of points.

4. A method according to claim 3, wherein each of said plurality of points is a search point at which said maximum amplitude of at least one of said peaks is detected.

5. A method according to claim 3, wherein said path includes a circumferential path in a bore in said body.

6. A method according to claim 3, wherein said path includes a helical path in a bore in said body.

7. A method for defining an extended flaw in a body, comprising:
scanning an ultrasonic transducer along a path on a surface on said body;
transmitting pulses of ultrasonic energy into said body from said transducer at a predetermined angle with respect to said surface;
receiving reflections of said ultrasonic energy at said surface along said path;
defining a group of peaks of reflections of ultrasonic energy received within a predetermined time and moving together in range during said scanning as originating along a surface of said extended flaw;
determining the points along said path at which ones of said peaks reach maximum amplitude; measuring a range from each of said points to a facet producing its maximum amplitude reflection; and
calculating positions of each of said facets in said body based on said predetermined angle, locations of said points and corresponding ranges to said facets, the facets defining points on said extended flaw.

8. A method according to claim 7, wherein said predetermined time is about 10 microseconds.

9. A method according to claim 8, wherein said predetermined time is about 5 microseconds.

10. A method according to claim 7, wherein the steps of transmitting and receiving are substantially collocated.

11. Apparatus for processing ultrasonic reflections from a body to define an extended flaw, in which transmitting and receiving transducers are moved in a scan on a surface of said body, comprising:
means for determining that a plurality of peaks of said ultrasonic reflections are received within a predetermined time;
means for correlating said peaks as said transmitting and receiving transducers are moved in said scan;
means for determining points along said path at which ones of said peaks are maximum; and
means for logging said points and ranges associated with said points, said points and ranges together with a predetermined propagation angle of ultrasonic energy in said body are usable to calculate positions of facets defining a surface of said extended flaw.

12. Apparatus according to claim 11, wherein said means for determining includes an A-scope display effective for displaying an amplitude versus time of said reflections.

13. Apparatus according to claim 11, wherein some of said means for determining, means for correlating and means for logging include a programmed digital computer.

14. A method for defining extended flaws in a specimen of the type having an axial bore therein, comprising:
scanning receiving and transmitting transducers of ultrasonic energy in one of a circumferential and an axial direction in said axial bore and incrementing said transducers in the other of said directions, said transmitting transducer propagating ultrasonic energy at a predetermined angle in said body;
measuring ranges of reflections of ultrasonic energy;
determining that a predetermined plurality of said reflections are within a predetermined distance of each other;
finding search positions of said transducers producing maximum amplitudes of individual ones of said reflections;
calculating positions of facets on said extended flaw based on said predetermined angle, said search positions and corresponding ranges; and
said facets defining said extended flaw.

15. A method according to claim 14, wherein said ultrasonic energy is in the shear mode.

* * * * *